(12) United States Patent
Yam

(10) Patent No.: US 6,773,715 B1
(45) Date of Patent: Aug. 10, 2004

(54) PREPARATION AND USE OF SOLIDIFIED OILS

(75) Inventor: Daniel Yam, Rishon LeZion (IL)

(73) Assignee: Yamega Ltd., Ramat Hasharon (IL)

( * ) Notice: Subject to any disclaimer, the term of this patent is extended or adjusted under 35 U.S.C. 154(b) by 0 days.

(21) Appl. No.: 09/830,357

(22) PCT Filed: Oct. 25, 1999

(86) PCT No.: PCT/IL99/00564
§ 371 (c)(1), (2), (4) Date: Jul. 17, 2001

(87) PCT Pub. No.: WO00/24360
PCT Pub. Date: May 4, 2000

(30) Foreign Application Priority Data

Oct. 25, 1998 (IL) .................................................. 126741

(51) Int. Cl.$^7$ ........................ A61K 47/00; A61K 31/20; A23D 7/00
(52) U.S. Cl. ........................ 424/439; 514/560; 426/608
(58) Field of Search ........................ 424/439; 514/560; 426/608

(56) References Cited

U.S. PATENT DOCUMENTS

| 3,102,814 A | 9/1963 | Thompson |
| 3,132,951 A | 5/1964 | Thompson |
| 3,253,927 A | 5/1966 | Going |
| 5,064,677 A | 11/1991 | Cain et al. |
| 5,130,151 A | 7/1992 | Averbach |
| 5,248,509 A | 9/1993 | Bruin |
| 5,268,186 A | * 12/1993 | Moskowitz ................... 426/93 |
| 5,472,728 A | 12/1995 | Miller et al. |
| 5,514,407 A | 5/1996 | Perlman et al. |
| 5,624,703 A | 4/1997 | Perlman et al. |
| 5,817,322 A | 10/1998 | Xu |
| 5,885,559 A | 3/1999 | Lee et al. |
| 5,908,377 A | 6/1999 | Fukuda |
| 6,020,020 A | * 2/2000 | Cain et al. ................... 426/601 |
| 6,099,866 A | 8/2000 | Slimak |
| 6,117,476 A | 9/2000 | Eger et al. |
| 6,123,979 A | 9/2000 | Hepburn et al. |
| 6,159,525 A | 12/2000 | Lievense et al. |
| 6,162,483 A | 12/2000 | Wester |

FOREIGN PATENT DOCUMENTS

| GB | 1146558 | * 3/1969 | |
| JP | 07292385 | * 11/1995 | ............ A23D/9/00 |

OTHER PUBLICATIONS

Nippon Grease, JP 56079194, 1981, Derwent Abstract, 1981–59619D.*
Ding, CN 1088800, 1994, Derwent Abstract, 1995–241288.*
Merck Index, Eleventh edition, 1989, p. 159.*

* cited by examiner

Primary Examiner—Shengjun Wang
(74) Attorney, Agent, or Firm—Browdy and Neimark, PLLC

(57) ABSTRACT

A method of solidifying liquid oils is disclosed. The method is effected by (a) mixing at least one liquid oil and at least one solid fat, thereby forming a mixture of the at least one liquid oil and the at least one solid fat; and (b) transforming the mixture into a homogeneous consistency. Further disclosed are compositions of matter having a semi-solid texture including at least one liquid oil and at least one solid fat and uses thereof in therapy and cosmetic applications.

9 Claims, 1 Drawing Sheet

Mean + SD lung weight of mice after resection of primary growth and under SO or FO diet

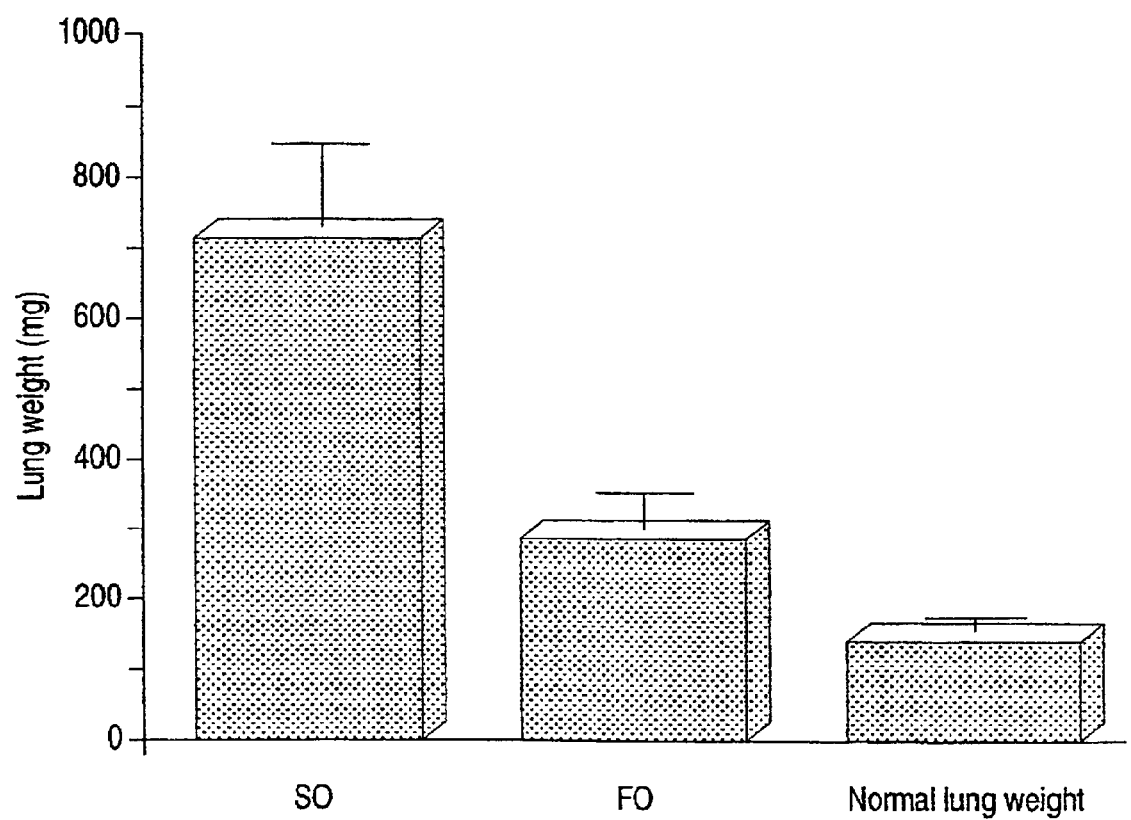
FIG.1. Mean + SD lung weight of mice after resection of primary growth and under SO or FO diet

PREPARATION AND USE OF SOLIDIFIED OILS

REFERENCE TO RELATED APPLICATIONS

The present application is the national stage under 35 U.S.C. 371 of international application PCT/IL99/00564, filed Oct. 25, 1999 which designated the United States, and which international application was published under PCT Article 21 (2) in the English language.

FIELD AND BACKGROUND OF THE INVENTION

The present invention relates to a method of solidifying at least one oil by the addition of at least one solid fat and, more particularly, to a method of forming a semi-sold paste containing a high concentration of an oil which is normally liquid. The present invention further relates to a soft solid mixture which typically includes 50% or more ethyl esters of natural fatty acids and 50% or less solid fat and, more particularly, to a semi-solid mixture containing fish oil or another source of fat soluble vitamins, including, but not limited to, purified vitamin E. The present invention further relates to a method of using an oil for purposes including, but not limited to, nutritional supplementation, cosmetic treatment, and medical treatment.

Most fats which are nutritionally important substances exist as fluid oils. Their handling, storage and application is therefore limited to containers (e.g., cooking oil) or capsules (e.g., vitamin E). In principle, such oils can be handled in a solidified form by the addition of large excess of solids like starch, calcium carbonate, lactose etc., which is a common practice in the pharmaceutical industry. After addition of solids, the oils may be pressed into tablets. Owing to the physical size limit of tablets or capsules designed to be consumed by humans, high dose therapy with purified vitamin E, or with substances such as wheat germ oil or fish oil has been problematic because treatment regimens require daily consumption of tens of tablets or capsules. Much of the problem stems not from the efficacy of the therapeutic oil, but from poor patient compliance with treatment protocols requiring intake of large numbers of tablets or capsules each day. The root of this compliance problem lies in the fact that preparation of soft-soled mixtures which contain dietary oil at a concentration above 50% while the solidifying agent is biologically compatible, are not taught by prior art.

There is increasing evidence that vitamin e, or fish oil which is rich in omega-3 polyunsaturated fatty acids ($\Omega$-3 PUFA), can be used advantageously to treat or prevent a wide range of conditions including, but not limited to, excess gastric acid secretion, blood clotting, arterial thrombogenesis, various types of cancer, hepatitis, depression, high blood pressure, and heart disease (Riber, C. et al., Scand. J. Gastroenterol. (1999) 34:845–8; Saldeen, T. et al., J. Am. Coll. Cardiol. (1999) 34:1208–15; Ferguson, L. R. Mutat. Res. (1999) 428:329–38; Look, M. P. et al., Antiviral Res. (1999) 43:113–22; Kolleck, I. et al. Free Radic. Biol. Med. (1999) 27:882–90; Shibata, H. et al., J. Epidemiol. (1999) 9:261–7; Cham, B. E. et al., Clin. Chim. Acta. (1999) 287:45–57; Yosefy, C. et al., Prostaglandins Leukot Essent Fatty Acids (1999) 61:83–7; Hardman, W. E. et al. Br. J. Cancer (1999) 81:440–8; Barber, M. D. B. M. J. (1999) 319(7203):187; Adams, A. K. et al., Am. Fam. Physician (1999) 60:895–904; Barber, M. D. et al., Br. J. Cancer (1999) 81:80–6; Latham, P. et al. Biochem. Soc. Trans. (1998) 26:S158; Bang, H. O. Compr. Ther. (1990) 16:31–5; Urakaze, M. et al. J. Hum. Hypertens. (1989) 3:277–8)

Unfortunately, many patients suffering from diseases which may be treated by nutritionally important oils suffer from nausea and reduced appetite. These patients are especially unlikely to comply with treatment protocols which include ingestion of large numbers of pills or tablets each day.

There is thus a widely recognized need for, and it would be highly advantageous to have, nutritionally or medically important oils at high concentration in a semisolid form in order to facilitate better patient compliance with proposed treatment regimens.

SUMMARY OF THE INVENTION

According to one aspect of the present invention there is provided a method of solidifying liquid oils, the method comprising the steps of (a) mixing at least one liquid oil and at least one solid fat, thereby forming a mixture of the at least one liquid oil and the at least one solid fat; and (b) transforming the mixture into a homogeneous consistency.

According to another aspect of the present invention there is provided a composition of matter comprising a mixture of at least one liquid oil and at least one solid fat.

According to yet another aspect of the present invention there is provided a composition of matter comprising a mixture of at least one ethyl ester of a natural fatty acid and at least one solid fat.

According to still another aspect of the present invention there is provided a method of using at least one liquid oil for a purpose selected from the group consisting of nutritional supplementation, cosmetic treatment, use as a food additive, medical treatment, medical prophylaxis and cosmetic prophylaxis, the method comprising the steps of using a composition of matter including a mixture of at least one liquid oil and at least one solid fat for accomplishing the purpose.

According to an additional aspect of the present invention there is provided a method of using at least one liquid oil for prevention or treatment of a medical condition selected from the group consisting of cancer, hypertriglyceridemia, hypo HDL, high cholesterol, hyperinsulinemia and hyperglycemia, the method comprising the step of using a composition of matter including a mixture of at least one liquid oil and at least one solid fat for accomplishing the prevention or treatment.

According to further features in preferred embodiments of the invention described below, the composition of matter has a homogeneous consistency.

According to still further features in the described preferred embodiments the at least one liquid oil is at least 50% of the mixture by weight.

According to still further features in the described preferred embodiments the composition of matter further comprising at least one additional ingredient.

According to still further features in the described preferred embodiments the at least one additional ingredient includes at least one flavoring agent.

According to still further features in the described preferred embodiments the at least one additional ingredient includes at least one odorant.

According to still further features in the described preferred embodiments the at least one solid fat is selected from a group of solid fats consisting of bee wax, propolis, butter, artificially hydrogenated vegetable oil, palm oil, cocoa butter, rendered animal fat and lanolin.

According to still further features in the described preferred embodiments the at least one solid fat is a synthetic polyester of fatty acids and a saccharide.

According to still further features in the described preferred embodiments the saccharide is selected from the group of saccharides consisting of sorbitol, glucose, fructose, lactose, mannose, ribose and deoxy-ribose.

According to still further features in the described preferred embodiments the at least one solid fat is a mixture of saccharide is sucrose and further wherein the fatty acid is selected from the group consisting of polypalmitate and polystearate.

According to still further features in the described preferred embodiments the at least one liquid oil includes omega-3 polyunsaturated fatty acids.

According to still further features in the described preferred embodiments the at least one liquid oil includes α-tocopherol (vitamin E).

The present invention successfully addresses the shortcomings of the presently known configurations by providing nutritionally or medically important liquid oils at high concentration in a semi-solid form in order to facilitate better patient compliance with proposed treatment regimens.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a bar-graph presenting the effect of consuming a bee wax solidified fish oil containing 60% Ω-3 PUFA according to the present invention on lung metastasis. Mice (C57BL/6J) were kept in filter-covered plastic cages (10 mice per cage) and were fed ad libitum with a basal oil-free standard diet supplemented with 5% by weight of either bee wax solidified fish oil (FO) or bee wax solidified soybean oil (SO). After two weeks mice were inoculated in the footpad with $5 \times 10^5$ cells of a highly metastatic clone (D 122) of the 3LL Lewis Lung Carcinoma cell line (Eisenbach, L. et al. Int. J. Cancer (1993) 32:113–120) per mouse in 50 µl sterile phosphate buffered saline (PBS). When primary tumor reached a diameter of 8–9 mm, as was determined using a Varnier caliber, the tumor bearing leg was removed by amputation after ligation above the knee joint. Twenty eight days after amputation the surviving mice were sacrificed and lungs were assessed for metastatic load by weighing.

DESCRIPTION OF THE PREFERRED EMBODIMENTS

The present invention is of methods for producing mixtures containing typically greater than 50% liquid oil(s) which are semi-solid or solid at room temperature and/or when refrigerated by household means. The present invention is further of compositions of matter containing typically greater than 50% liquid oil which are semi-solid or solid at room temperature and/or when refrigerated by household means. The present invention is further of methods of medical treatment, prophylaxis, nutritional supplementation or cosmetic treatment which employ compositions of matter containing greater than 50% oil which are semi-solid or solid at room temperature and/or when refrigerated by household means. Specifically, the present invention can be used to increase patient compliance in therapy regimens requiring consumption of large quantities of oil by allowing preparation and presentation of the material to be ingested in a small volume and in a more palatable form than previously available.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For purposes of this specification and the accompanying claims, the term "liquid oil" refers to an oil which is a liquid in at least a portion of the temperature range of 4–25° C.

For purposes of this specification and the accompanying claims, the term "solid fat" refers to an oil which is a solid in at least a portion of the temperature range of 4–25° C.

For purposes of this specification and the accompanying claims, the term "vegetable oil" refers to any oil derived from any part of a plant, including, but not limited to, soybean oil, corn oil, rapeseed oil, olive oil, yam oil, cottonseed oil, walnut oil, peanut oil and almond oil.

For purposes of this specification and the accompanying claims, the term "artificially hydrogenated" refers to any process by which the degree of saturation of carbon to carbon double bonds may be increased, whether mechanically, physically, or chemically.

As shown in Example 1 below, one preferred embodiment of the present invention is solidification of fish oil by bee wax to produce a mixture containing about 80% Ω-3 PUFA. A patient requiring a daily dose of 6 grams of Ω-3 PUFA would therefore need to consume 10–12 grams of the resultant semi-solid paste. This portion of semi-solid paste would take the place of, for example, 20 capsules which typically contain about 300 mg Ω-3 PUFA.

A 10–12 gram portion of solidified fish oil paste could be ingested, for example, by spreading it upon a single slice of bread. According to alternate embodiments, the semi-solid paste might be mixed with flavoring agents, including, but not limited to, smoked salmon flavor, or parmesan cheese flavor, to render it more palatable. Alternately, odorants, such as garlic scent or oregano scent might be added to increase palatability.

As shown in Example 4 below, purified vitamin E may be similarly solidified by combining it with a low calorie fat substitute. Advantages of using a low calorie fat substitute in compositions of matter of the present invention include, but are not limited to, keeping total caloric intake of a patient as low as possible.

Myriad medical conditions may be treated using oils as dietary supplements. Examples 5 and 6 describe treatment of a cancer (in an animal model) and hyperlipidemia, respectively. These embodiments are presented as examples of a wide range of possible benefits from the present invention.

Example 5 describes reduced tumor growth, mortality and metastatic growth in a well established murine lung cancer model in response to dietary supplementation with solidified fish oil prepared according to the method of the present invention. Extrapolation of the results to human patients suggests tremendous potential benefit. With respect to cancer patients, the method of the present invention is especially important, since these patients tend to suffer from decreased appetite and nausea. It is therefore especially important to increase palatability of medication in order to elicit compliance with a proposed treatment regimen.

Example 6 describes the effects of administration of solidified fish oil according to the present invention to human subjects to control hyperlipidemia. After 6 weeks, treatment induced a significant reduction in triglycerides, cholesterol, insulin and glucose was observed. A concurrent increase in HDL and decrease in cholesterol values was achieved. Since this type of treatment must be on going in order to be medically effective, issues of patient compliance in the long run are critical. Increasing palatability of a medicine, or presenting together with food, are important in this context too.

Thus, according to one aspect of the present invention there is provided a method of solidifying liquid oils. The method according to this aspect of the present invention is effected by mixing at least one liquid oil and at least one solid fat, thereby forming a mixture of same and further by transforming the mixture into a homogeneous consistency.

According to another aspect of the present invention there is provided a composition of matter which includes a mixture of at least one liquid oil and at least one solid fat.

According to yet another aspect of the present invention there is provided a composition of matter which includes a mixture of at least one ethyl ester of a natural fatty acid (which is a liquid oil) and at least one solid fat.

According to still another aspect of the present invention there is provided a method of using at least one liquid oil for a purpose, such as, but not limited to, nutritional supplementation, cosmetic treatment, use as a food additive, medical treatment, medical prophylaxis and/or cosmetic prophylaxis. The method according to this aspect of the present invention is effected by using a composition of matter including a mixture of at least one liquid oil and at least one solid fat for accomplishing the purpose. The use may include, but is not limited to, ingestion and/or external application.

According to an additional aspect of the present invention there is provided a method of using at least one liquid oil for prevention or treatment of a medical condition such as, but not limited to, cancer, hypertriglyceridemia, hypo HDL, high cholesterol, hyperinsulinemia and/or hyperglycemia. The method according to this aspect of the present invention is effected by using a composition of matter including a mixture of at least one liquid oil and at least one solid fat for accomplishing the prevention or treatment. The use may include, but is not limited to, ingestion and/or external application.

According to a preferred embodiment of the present invention the composition of matter has a homogeneous consistency. Such homogeneous consistency can be achieved by, for example, heating the mixture of oil and fat to a temperature above the melting temperature of the fat, e.g., 40–100° C., and thereafter gradually cooling the mixture to room temperature.

According to preferred embodiments of the present invention the liquid oil(s), which is the constituent of therapeutic value, is at least 50%, preferably at least 60%, more preferably, at least 70%, most preferably at least 80% of the solidified mixture by weight. It will however be appreciated that sufficient percentage of fat(s) should be employed to achieve solidification at at least a portion of the temperature range of 4° C. and 25° C.

The composition of matter according to preferred embodiments of the present invention preferably includes in addition to oil(s) and fat(s) at least one additional ingredient, such as but not limited to, at least one flavoring agent and/or at least one odorant. Extracts of such flavoring agents and odorants are well known in the art. Such agents or odorants come in many forms ranging from powders to liquid extracts. They are typically used in minute quantities, typically fractions of percents up to a few percents by weight, to alter a taste and/or the odor of foods.

The solid fat(s) can be on any type which complies with the above definition, such as, but not limited to bee wax, propolis, butter, artificially hydrogenated vegetable oil, palm oil, cocoa butter, rendered animal fat and/or lanolin. Alternatively or in addition the solid fat can include asynthetic polyester of fatty acids and a saccharide, such as, but not limited to, sorbitol, glucose; fructose, lactose, mannose, ribose or deoxy-ribose. The fatty acid is preferably polypalmitate and polystearate, whereas the sarcharide is preferably sucrose.

The liquid oil(s) fraction of the solidified mixture according to the present invention preferably includes substantial amounts, say 20–90% by weight, of omega-3 polyunsaturated fatty acids. Thus, the liquid oil employed can be omega-3 polyunsaturated fatty acids enriched fish oil, e.g., above 50%, preferably about 80% by weight omega-3 polyunsaturated fatty acids. Thus, the liquid oil employed can be Ω-3PUFA enriched fish oil.

Alternatively, the liquid oil(s) fraction of the solidified mixture according to the present invention preferably includes substantial amounts, say 20–90% by weight, of atocopherol (vitamin E).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Generally, the nomenclature used herein and the laboratory procedures in described below are those well known and commonly employed in the art. Other general references are provided throughout this document. The procedures therein a re believed to be well known in the art and are provided for the convenience of the reader. All the information contained therein is incorporated herein by reference.

Example 1
Solidification of Fish Oil by Bee Wax

Eighty grams of bee wax (Colmeia do Mato Grosso, Mato Grosso, Brasil) was warmed to 80° C. and mixed, under a nitrogen atmosphere with 400 grams fish oil (EPAX7010 triglycerides, Pronova Biocare a.s. Sandefjord, Norway). The mixture was mechanically stirred until a homogeneous consistency was obtained. Upon cooling to 25° C., the mixture solidified to form a homogeneous semi-solid paste. The weight percent of the fish oil in this mixture is 83%. This material was subsequently employed in Examples 5 and 6.

Example 2

Solidification of Soybean Oil by Bee Wax

A Eighty grams of bee wax (Colmeia do Mato Grosso, Mato Grosso, Brasil) was warmed to 80° C. and mixed, under a nitrogen atmosphere with 400 grams soybean oil (from the market). The mixture was mechanically stirred until a homogeneous consistency was obtained. Upon cooling to 25° C., the mixture solidified to form a homogeneous semi-solid paste. The weight percent of the oil in this mixture is 80%. This material was subsequently employed as control in Example 5.

Example 3

Solidification of Soybean Oil by Bee Wax

Eighty grams of bee wax (Colmeia do Mato Grosso, Mato Grosso, Brasil) was warmed to 80° C. and mixed, under a nitrogen atmosphere with 400 grams olive oil (from the market). The mixture was mechanically stirred until a homogeneous consistency was obtained. Upon cooling to 25° C., the mixture solidified to form a homogeneous semi-solid paste. The weight percent of the oil in this mixture is 80%. This material was subsequently employed as control in Example 6.

Example 4

Solidification of α-tocopherol (Vitamin E) by Sucrose Polyester

Ten grams of a-tocopherol (vitamin E, Sigma, St. Louis, Missouri) was mixed with 2 grams sucrose polyester (Olestra; Procter and Gamble, Mason, Ohio) and warmed to 80° C. under a nitrogen atmosphere to produce a homogeneous mixture. Upon cooling to room temperature the mixture solidified. The weight percent of vitamin E in this mixture is 83%.

Example 5

Treatment of Tumor Bearing Mice with Solidified Fish Oil

Using previously published methods for monitoring tumor progression and metastatic growth (Yam et al. Nutritional Bioch. (1979) 8:619–622) the effect of solidified fish oil prepared as is described under Example 1 on mice (C57BL/6J) bearing a well characterized Lewis Lung Carcinoma (3LL) was studied in comparison to control mice of the same strain and to mice (C57BLU6J) bearing the well characterized Lewis Lung Carcinoma (3LL) fed with solidified soybean oil as is described under Example 2

All mice were kept in filter-covered plastic cages (10 mice per cage) and were fed ad libitum with a basal oil-free standard diet supplemented with 5% by weight of either bee wax solidified fish oil (FO) or bee wax solidified soybean oil (SO).

After two weeks of ad libitum feeding with these diets, tumor inoculation was conducted using a highly metastatic clone (D 122) of the 3LL Lewis Lung Carcinoma cell line (Eisenbach, L. et al. Int. J. Cancer (1993) 32:113–120). To this end, mice were inoculated in the footpad with $5 \times 10^5$ cells per mouse in 50 µl sterile phosphate buffered saline (PBS). Tumor size was monitored with a Varnier caliber. As described by Eisenbach et al., when local tumor reached a diameter of 8–9 mm, the tumor bearing leg was removed by amputation after ligation above the knee joint. Twenty eight days after amputation the surviving mice were sacrificed and lungs were assessed for metastatic load by weighing and further by histological examination.

Significantly slower growth of primary tumor, lower mortality rate and lower metastatic spread were observed in mice fed with fish oil (FO) in comparison with mice fed with soybean oil (SO). The results of lung weights are summarized in FIG. 1.

Example 6

Treatment of Patients with Hyperlipidemia with Solidified Fish Oil

Patients and methods: 21 ambulatory patients, age 48–71 y (15 men and 6 women) with hyperlipidemia were divided in two groups (test and control groups), took part in this study. The test group (10 men and 2 women) consumed 5 grams per day of solidified fish oil in the form described under Example 1 above, while the control group (7 patients) consumed the same amount of an isocaloric placebo in which the fish oil was replaced by olive oil as described under Example 3 above. Fasting blood samples were drawn at 0 and 42 days for analysis (see table 1 below).

Blood analysis: Part of the blood was transferred to precooled centrifuge tubes containing fluoride-oxalate and centrifuged at 1,500 r.p.m. for 10 minutes and plasma was collected and frozen.

Triglycerides were determined by an enzymatic procedure with a commercial kit (Triglycerides Enzymatiques PAP 1000, Bio-Merieux, Charbonnieres-les-Bains, France).

Total cholesterol was determined in serum by an enzymatic calorimeter method according to Siedel et al. (Clin. Chem. (1983) 29:1075) using a commercially available kit (Monotest Cholesterol, Bohringer Diagnostica, GmbH, Mannheim, FRG).

High-density lipoprotein (HDL) was analyzed according to Lopes-Virella et al. (Clin. Chim. (1977) 23:882).

Insulin level was determined in the serum by a double antibody radioimmunoassay, using $^{125}$I-labeled human insulin (Pharmacia Diagnosis AB, Uppsala, Sweden).

Glucose was determined according to Pennock et al. (Clin. Chi. Acta. (1973) 48:193).

The results are summarized in Table 1 below.

TABLE 1

Values* of plasma triglycerides, cholesterol, LDL-cholesterol insulin and glucose at day 0 and after 42 days

| | TEST GROUP | | CONTROL GROUP | |
|---|---|---|---|---|
| | 0 days | 42 days | 0 days | 42 days |
| Triglycerides (mg/dl) | 240 ± 39 | 180 ± 18 | 230 ± 35 | 220 ± 42 |
| Cholesterol (mg/dl) | 270 ± 34 | 230 ± 19 | 280 ± 36 | 260 ± 28 |
| HDL-cholesterol (mg/dl) | 30 ± 12 | 48 ± 16 | 32 ± 15 | 35 ± 17 |
| Insulin (µU/ml) | 31 ± 13 | 18 ± 8 | 30 ± 14 | 31 ± 17 |
| Glucose (mg/dl) | 142 ± 18 | 95 ± 15 | 128 ± 22 | 126 ± 22 |

*Mean ± S.D.

The results of the blood biochemistry presented in Table 1 above indicate that the solidified fish oil treatment induced a significant reduction in triglycerides, cholesterol, insulin and glucose and an increase in HDL-cholesterol values after 42 days of treatment. No significant changes were observed in the control group. No negative side effects were observed in either group.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A homogeneous semi-solid paste for spreading consisting essentially of at least 50% by weight of fish oil and 50% or less of beeswax.

2. A homogeneous semi-solid paste for spreading according to claim 1 consisting essentially of at least about 80% by weight of fish oil.

3. A homogeneous semi-solid paste for spreading according to claim 2 wherein the amount of omega-3 polyunsaturated fatty acids in said fish oil is such that said composition comprises about 60% by weight of omega-3 polyunsaturated acids.

4. A homogeneous semi-solid paste for spreading, consisting essentially of at least about 80% by weight of fish oil with the remainder being beeswax and at least one additional ingredient selected from the group consisting of odorants and flavoring agents.

5. A homogeneous semi-solid paste for spreading according to claim 2, consisting essentially of at least about 80% by weight of fish oil, with the remainder being beeswax and at least one additional ingredient selected from the group consisting of odorants and flavoring agents.

6. A homogeneous semi-solid paste for spreading according to claim 5, wherein said at least one flavoring agent is smoked salmon flavor or parmesan cheese flavor.

7. A homogeneous semi-solid paste for spreading according to claim 5, wherein said at least one odorant is garlic scent or oregano scent.

8. A method for the preparation of a homogeneous semi-solid paste suitable for spreading and consisting essentially of from about 50% to about 80% by weight of fish oil, and beeswax, said method comprising:

(a) mixing fish oil with beeswax at 80° C. under stirring until a homogeneous consistency is obtained; and (b) cooling said mixture to room temperature, thus obtaining a homogeneous semi-solid paste containing from at least about 50% to about 80% by weight of fish oil, that can be stored at room temperature and/or by household refrigeration.

9. A method for the preparation of homogeneous semi-solid paste suitable for spreading consisting essentially of about 83% by weight of fish oil, said method comprising:

(a) mixing 400 g fish oil with 80 g beeswax at 80° C. under stirring until a homogeneous consistency is obtained; and (b) cooling said mixture to room temperature, thus obtaining a homogeneous semi-solid paste containing about 83% by weight of fish oil that can be stored at room temperature and/or by refrigeration.

* * * * *